US005683705A

United States Patent [19]
Maes et al.

[11] Patent Number: 5,683,705
[45] Date of Patent: Nov. 4, 1997

[54] SULFUR-BASED AMIDES AND BIS-AMIDES USEFUL AGAINST SKIN DISORDERS

[75] Inventors: Daniel H. Maes, Huntington, N.Y.; Jules Zecchino, Closter; Althea Knight, Teaneck, both of N.J.

[73] Assignee: Estee Lauder, Inc., New York, N.Y.

[21] Appl. No.: 626,769

[22] Filed: Mar. 29, 1996

[51] Int. Cl.⁶ .......................... A61K 7/48; C07C 233/00
[52] U.S. Cl. .................. 424/401; 514/622; 514/625; 514/629; 514/852; 514/859; 514/863; 514/944; 564/177; 564/179; 564/201; 564/203
[58] Field of Search .................. 424/401; 514/622, 514/625, 629, 852, 859, 863, 944; 564/177, 179, 201, 203

[56] References Cited

U.S. PATENT DOCUMENTS

| | | | |
|---|---|---|---|
| 3,879,537 | 4/1975 | Van Scott et al. | 424/311 |
| 3,920,835 | 11/1975 | Van Scott et al. | 424/311 |
| 3,968,218 | 7/1976 | Bouillon et al. | 424/267 |
| 3,984,566 | 10/1976 | Van Scott et al. | 424/283 |
| 3,988,470 | 10/1976 | Van Scott et al. | 424/283 |
| 4,089,942 | 5/1978 | Boré et al. | 424/267 |
| 4,105,782 | 8/1978 | Yu et al. | 424/283 |
| 4,105,783 | 8/1978 | Yu et al. | 424/47 |
| 4,194,007 | 3/1980 | Van Scott et al. | 424/283 |
| 4,197,316 | 4/1980 | Yu et al. | 424/283 |
| 4,234,599 | 11/1980 | Van Scott et al. | 424/318 |
| 4,246,261 | 1/1981 | Van Scott et al. | 424/317 |
| 4,363,815 | 12/1982 | Yu et al. | 424/279 |
| 4,380,549 | 4/1983 | Van Scott et al. | 424/274 |
| 4,542,129 | 9/1985 | Orentreich | 514/178 |
| 5,091,171 | 2/1992 | Yu et al. | 424/642 |
| 5,155,106 | 10/1992 | Shimizu et al. | 514/227.5 |
| 5,254,343 | 10/1993 | Parab et al. | 424/401 |
| 5,262,407 | 11/1993 | Leveque et al. | 514/159 |
| 5,334,377 | 8/1994 | Junino et al. | 424/71 |

FOREIGN PATENT DOCUMENTS

| | | |
|---|---|---|
| WO 93/10756 | 6/1993 | WIPO . |
| WO 94/05302 | 3/1994 | WIPO . |

OTHER PUBLICATIONS

Barnett, "Analogues of Panthothenic Acid. Part III. Preparation of Growth–Inhibiting Analogues Related to N–Pantoylaurine".

Cox et al., "Pyochelin: Novel Structure of an Iron–Chelating Growth Promoter for Pseudomonas Aeruginosa", Proc. Natl. Acad. Sci. USA 78(7):4256–4260 (1981).

Mills et al, "The Synthesis of Some New Pyrimidines and Uric Acids from Cystamines", J. Am. Chem. Soc. 62:1173–1180 (1940).

*Primary Examiner*—Jyothsan Venkat
*Attorney, Agent, or Firm*—Pennie & Edmonds LLP

[57] ABSTRACT

Novel sulfhydryl group-containing amides and disulfide group-containing bis-amides useful for treating or preventing an abnormal biological condition or a disease, and/or improving the texture or appearance of the skin, as well as compositions containing amides and bis-amides and methods for their use are described. Such types of abnormal biological conditions or diseases include skin atrophy, i.e., the thinning and/or general degradation of the dermis often characterized by a decrease in collagen and/or elastin as well as decreased number, size and doubling potential of fibroblast cells, and other maladies including, but are not limited to dry skin, severe dry skin, dandruff, acne, keratoses, psoriasis, eczema, skin flakiness, pruritus, age spots, lentigines, melasmas, wrinkles, warts, blemished skin, hyperpigmented skin, hyperkeratotic skin, inflammatory dermatoses, age-related skin changes and skin in need of cleansers.

18 Claims, No Drawings

SULFUR-BASED AMIDES AND BIS-AMIDES USEFUL AGAINST SKIN DISORDERS

FIELD OF THE INVENTION

This invention relates to novel sulfhydryl group-containing amides and disulfide group-containing bis-amides useful for treating or preventing abnormal skin conditions or diseases, and/or improving the texture or appearance of the skin, to pharmaceutical or cosmetic compositions containing the sulfhydryl group-containing amides and disulfide group-containing bis-amides and to methods for the use of the compounds and compositions.

BACKGROUND OF THE INVENTION

Hydroxybenzoic acids and α-hydroxycarboxylic acids (known as "AHAs") have been used to treat skin conditions for over several decades. For example, α-hydroxycarboxylic acids have been used to treat ichthyosis, hyperkeratoses, dandruff and ache (see, U.S. Pat. Nos. 3,879,537 to Van Scott et al.; 3,920,835, 3,988,470, and 4,234,599 to Van Scott et al.; 3,984,566 to Van Scott et al.; and 4,105,782 to Yu et al.; respectively). α-Hydroxycarboxylic acids have also been used to treat dry skin (see, U.S. Pat. Nos. 4,105,783 to Yu et al.; 4,194,007 to Van Scott et al.; 4,197,316 to Yu et al.; 4,380,549 to Van Scott et al.; 4,363,815 to Yu et al. and 5,091,171 to Yu et al. α-Hydroxycarboxylic acids have also been used to enhance the antiinflammatory action of corticosteroids (see, U.S. Pat. No. 4,246,261 to Van Scott et al.). U.S. Pat. No. 5,254,343 to Parah et al. discloses the use of salts of α-hydroxyacids in conjunction with steroids to minimize cutaneous atrophy, a side-effect of steroid application to the skin. U.S. Pat. No. 4,542,129 to Orentreich teaches the use of a mixture of a keratolytic agent, such as a hydroxybenzoic acid or an α-hydroxycarboxylic acid, and dehydroepiandrosterone to treat dry skin while deterring acne formation.

Salicylic acid has also been used to treat conditions of the skin. International Publication No. WO 93/10756, published Jun. 10, 1993 to Blank teaches the use of salicylic acid to regulate wrinkles and/or atrophy in mammalian skin. U.S. Pat. No. 5,262,407 to Leveque et al. teaches the use of $C_1$–$C_{18}$ alkanoyl 5-acylsalicylic acids to treat aging skin.

One of the drawbacks of using α-hydroxyacids or hydroxybenzoic acids, such as salicylic acid, for treating persons having skin ailments, however, is that at high concentrations, such acids are known to remove the outer layer of skin by chemically burning the skin off the patient. Such treatments are known in the art as "chemical peels." However, when improperly monitored, chemical peeling of the outer layer of skin using these acids can lead to inflammation, infection and scarring. In addition, α-hydroxyacids are known to cause skin irritation at certain lower levels in some individuals. Thus, there is a need for a composition capable of providing the skin-healing benefits of α-hydroxyacids or hydroxybenzoic acids, such as salicylic acid, while avoiding the drawbacks such as those described above.

Hydroxylated thioethers also been used to treat skin ailments. For example, U.S. Pat. No. 3,968,218 to Bouillon et al. discloses the use of hydroxylated amino thioethers for treating greasy skin.

Cysteamine derivatives have been used on the skin and scalp. FR 1,505,874 to Kalopissis discloses the use of s-benzylcysteamines for the treatment of seborrhea and acne. U.S. Pat. No. 4,089,942 to Boré et al. discloses deodorant compositions for body hygiene comprising S-benzylcysteamine or an organic salt thereof. U.S. Pat. No. 5,334,377 to Junino et al. discloses the use of cysteamine amides of aminoacids as reducing agents useful in a process for the permanent deformation of the hair. None of the above references suggest the use of sulfhydryl group-containing amides or disulfide group-containing bis-amides for treating or preventing abnormal skin conditions or diseases, and/or improving the texture or appearance of the skin. Moreover, none of the above references suggest the use of a compound which possesses the benefits of α-hydroxy or salicylic acids while avoiding their undesirable side effects. Thus, there is a need for cosmetic and pharmaceutical compositions with skin moisturizing and/or healing properties of α-hydroxycarboxylic and salicylic but without their deleterious effects.

German Patent Publication DE 1643487 discloses methods of synthesis useful for preparing various salts of S-substituted cysteamines.

PCT Publication No. WO 94/05302 to McCallum discloses the use of compositions comprising salicylic acid, elemental sulfur and cysteamine to treat "housewife dermatitis."

However, when compositions comprising more than one agent useful for treating skin are intended to be formulated, solvents or vehicles which successfully dissolve or suspend one of the necessary agents may be completely ineffective in dissolving or suspending the other(s), and vice versa. This can result in an excessive amount of time, energy and manpower required for determining the proper formulation solvents or vehicles. Further, chemical interactions among the one or more agents in a single formulation may render each agent inactive, or simply antagonize their activity. Thus, there remains a need for such a composition which can be efficiently formulated and/or which utilizes the advantages of one or more agents useful for treating skin.

As described below, the present invention provides novel compounds useful for treating or preventing abnormal skin conditions or diseases, and/or improving the texture or appearance of the skin with enhanced skin-healing properties. It further provides compounds which have the advantages of α-hydroxycarboxylic and salicylic acids without the above-mentioned biological disadvantages or formulation problems.

Additionally, the invention provides compositions comprising compounds having the advantages of α-hydroxycarboxylic and salicylic acids without the above-mentioned drawbacks.

SUMMARY OF THE INVENTION

The present invention provides novel sulfhydryl group-containing amides and disulfide group-containing his (amides) useful in treating or preventing abnormal skin conditions or diseases and/or improving the texture or appearance of the skin. Also encompassed are compositions comprising the sulfhydryl group-containing amides, the disulfide group-containing bis(amides) or mixtures thereof, said compositions being particularly suited for topical application. Finally, the invention includes methods for treating or preventing an abnormal biological skin condition, and improving the texture or appearance of the skin using the compositions described herein.

In particular, the invention encompasses sulfhydryl group-containing amides, useful for treating or preventing abnormal skin conditions or diseases and/or improving the texture or appearance of the skin, having the structure of formula I:

R—NH—Z—SH     (I)

and pharmaceutically or cosmetically acceptable salts thereof, wherein:

R is selected from the group consisting of (A)(A)C(OH)—C(O)— and 2-(HO)$C_6H_4$C(O)—; wherein each A is independently selected from the group consisting of hydrogen, phenyl and a $C_1$–$C_{22}$ alkyl or alkenyl group, said $C_1$–$C_{22}$ alkyl or alkenyl group being optionally substituted with one or more $C_1$–$C_4$ alkyl groups, phenyl, halogen or hydroxyl groups, said phenyl being optionally substituted with one or more $C_1$–$C_4$ alkyl, halogen, hydroxyl groups or methoxyl groups; and Z is selected from the group consisting of $C_2$–$C_{12}$ alkyl, $C_2$–$C_{12}$ alkenyl and $C_2$–$C_{12}$ alkynyl.

In a preferred embodiment of the invention, R is selected from the group consisting of 2-hydroxyethanoyl, 2-hydroxypropanoyl, 2-methyl-2-hydroxypropanoyl, 2-hydroxybutanoyl, 2-hydroxypentanoyl, 2-hydroxynonanoyl, 2-hydroxydecanoyl, 2-hydroxyoctanoyl, 2-hydroxydodecanoyl, 2-hydroxytetradecanoyl, 2-hydroxyhexadecanoyl, 2-hydroxyoctadecanoyl, 2-hydroxyeicosanoyl, 2-hydroxyphenyl-2-hydroxyethanoyl, 2,2-diphenyl-2-hydroxyethanoyl, 3-phenyl-2-hydroxypropanoyl, 2-phenyl-2-methyl-2-hydroxyethanoyl, 2-(4'-chlorophenyl)-2-hydroxyethanoyl, 2-(4'-hydroxy-3'methoxyphenyl)-2-hydroxyethanoyl, 3-(2'-hydroxyphenyl)-2-hydroxypropanoyl, 3-(4'-hydroxyphenyl)-2-hydroxypropanoyl, 2-(3',4'-dihydroxyphenyl)-2-hydroxyethanoyl, and salicylyl, wherein A is defined above; and Z is $C_2$–$C_6$ alkyl, most preferably $C_2$ alkyl.

Most preferred compounds of formula I are:
N-(salicylyl)cysteamine;
N-(lactyl)cysteamine;
N-(2-hydroxyoctanoyl)cysteamine;
N-(2-hydroxydecanoyl)cysteamine; and
N-(2-hydroxydodecanoyl)cysteamine.

It is to be understood that the compounds of formula I are alternatively represented by the structure of formula II:

(A)(A)C(OH)—C(O)—NH—Z—SH     (II)

wherein A and Z are defined above; and by the structure of formula III:

2-(HO)$C_6H_4$C(O)—NH—Z—SH     (III)

wherein Z is defined above.

In a further aspect of the invention, the invention encompasses disulfide group-containing bis-amides, useful in treating or preventing abnormal skin conditions or diseases and/or improving the texture or appearance of the skin, having the structure of formula IV:

R—NH—Z—S—S—Z—NH—R     (IV)

and pharmaceutically or cosmetically acceptable salts thereof, wherein:

each R is independently selected from the group consisting of (A)(A)C(OH)—C(O)— and 2-(HO)$C_6H_4$C(O)—, wherein each A is independently selected from the group consisting of hydrogen, phenyl and a $C_1$–$C_{22}$ alkyl or alkenyl group, said $C_1$–$C_{22}$ alkyl or alkenyl group being optionally substituted with one or more $C_1$–$C_4$ alkyl groups, phenyl, halogen or hydroxyl groups, said phenyl being optionally substituted with one or more $C_1$–$C_4$ alkyl, halogen, hydroxyl groups or methoxyl group; and each Z is independently selected from the group consisting of $C_2$–$C_{12}$ alkyl, $C_2$–$C_{12}$ alkenyl and $C_2$–$C_{12}$ alkynyl.

In a preferred embodiment of the invention, each R is independently selected from the group consisting of 2-hydroxyethanoyl, 2-hydroxypropanoyl, 2-methyl-2-hydroxypropanoyl, 2-hydroxybutanoyl, 2-hydroxypentanoyl, 2-hydroxynonanoyl, 2-hydroxydecanoyl, 2-hydroxyoctanoyl, 2-hydroxydodecanoyl, 2-hydroxytetradecanoyl, 2-hydroxyhexadecanoyl, 2-hydroxyoctadecanoyl, 2-hydroxyeicosanoyl, 2-hydroxyphenyl-2-hydroxyethanoyl, 2,2-diphenyl-2-hydroxyethanoyl, 3-phenyl-2-hydroxypropanoyl, 2-phenyl-2-methyl-2-hydroxyethanoyl, 2-(4'-chlorophenyl)-2-hydroxyethanoyl, 2-(4'-hydroxy-3'methoxyphenyl)-2-hydroxyethanoyl, 3-(2'-hydroxyphenyl)-2-hydroxypropanoyl, 3-(4'-hydroxyphenyl)-2-hydroxypropanoyl, 2-(3',4'-dihydroxyphenyl)-2-hydroxyethanoyl, and salicylyl; and each Z is preferably $C_2$–$C_6$ alkyl, most preferably $C_2$ alkyl.

Most preferred compounds of formula IV are:
N,N'-Bis(salicylyl)cystamine;
N,N'-Bis(lactyl)cystamine;
N,N'-Bis(2-hydroxyoctanoyl)cystamine;
N,N'-Bis(2-hydroxydecanoyl)cystamine; and
N,N'-Bis(2-hydroxydodecanoyl)cystamine.

It is to be understood that the compounds of formula IV are alternatively represented by the structure of formula V:

(A)(A)C(OH)—C(O)—NH—Z—S—S—Z—NH—C(O)—(HO)C(A)(A)     (V)

wherein A and Z are defined above; and by the structure of formula VI:

2-(HO)$C_6H_4$C(O)—NH—Z—S—S—Z—NH—(O)C$C_6H_4$-2-(OH)     (VI)

wherein Z is defined above.

In further embodiments, the invention encompasses cosmetic and pharmaceutical compositions containing one or more compounds of formula I or formula IV, or a pharmaceutically or cosmetically acceptable salt thereof, and a pharmaceutically or cosmetically acceptable carrier or excipient.

It is to be pointed out that the pharmaceutical compositions of the present invention are those which, when administered to the skin, render a benefit or an effect of treating or preventing an abnormal biological condition or a disease. Benefits or effects of treating or preventing such abnormal condition or disease are the reduction in severity or disappearance of the abnormal condition or disease. The reduction in severity or disappearance of the abnormal condition or disease may be either in the short- or long-term. Such abnormal biological conditions or diseases to be treated by administering a composition of the present invention include, but are not limited to dry skin, severe dry skin, dandruff, acne, keratoses, psoriasis, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers, as well as the effects of skin atrophy.

It is to be further pointed out that the cosmetic compositions of the present invention are those which, when administered to the skin, improve the texture or appearance thereof, without necessarily rendering a benefit or an effect of treating or preventing an abnormal biological condition or a disease. In this context, improving the texture or appearance of the skin is meant to encompass enhancing the skin's natural look and/or feel so as to increase the beauty and/or smoothness of the skin from its pre-treated state, or to mask unwanted symptoms of an abnormal biological condition or a disease. This can include providing a temporary moisturizing effect to the epidermis of the skin. Such abnormal biological conditions or diseases include, but are not limited to dry skin, severe dry skin, dandruff, acne, keratoses, psoriasis, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers, as well as the effects of skin atrophy.

In a still further embodiment, the invention encompasses methods for regulating skin atrophy comprising administering to a subject a safe and effective amount of one or more compounds of formula I or formula IV, or a pharmaceutically or cosmetically acceptable salt thereof, as described herein.

In yet another embodiment, the invention encompasses methods for regulating skin atrophy comprising administering to a subject a safe and effective amount of a composition comprising one or more compounds of formula I or formula IV, or a pharmaceutically or cosmetically acceptable salt thereof and a pharmaceutically or cosmetically acceptable carrier or excipient.

In yet another embodiment, the invention encompasses methods for treating disorders including but not limited to dry skin, severe dry skin, dandruff, acne, keratoses, psoriasis, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers.

The compounds of the present invention surprisingly demonstrate pharmaceutical activity or cosmetic effects against skin disorders heretofore not achieved by α-hydroxycarboxylic or salicylic acids themselves or by the combination of α-hydroxycarboxylic or salicylic acids with sulfur-containing compounds such as cysteamine and cystamine.

The present invention may be understood more fully by reference to the detailed description and illustrative examples which are intended to exemplify non-limiting embodiments of the invention.

DETAILED DESCRIPTION OF THE INVENTION

Definitions

As used herein, "skin atrophy" means the thinning and/or general degradation of the dermis layer of mammalian skin often characterized by a decrease in collagen and/or elastin as well as decreased number, size and doubling potential of fibroblast cells. Skin atrophy is a natural result of aging. Skin atrophy may be caused by either intrinsic or extrinsic factors such as natural chronoaging, photodamage, burns or chemical damage, or by exposure to pollutants or allergens, e.g., cigarette smoke. Skin atrophy is often an undesirable side effect resulting from treatment with α-hydroxycarboxylic or salicylic acids.

As used herein, "regulating skin atrophy" means preventing, retarding, arresting, treating or reversing the process of atrophy in mammalian skin.

As used herein, "safe and effective amount" means an amount of compound or composition sufficient to significantly induce a positive modification in the condition to be treated, but low enough to avoid serious side effects (at a reasonable benefit/risk ratio), within the scope of sound medical judgment. The safe and effective amount of the compound or composition will vary with the particular condition being treated, the age and physical condition of the patient being treated, the severity of the condition, the duration of the treatment, the nature of concurrent therapy, the specific compound, compounds or composition employed, the particular pharmaceutically-acceptable carrier utilized, and like factors within the knowledge and expertise of the attending physician or health care provider.

As used herein, "amide" means any compound of formula I wherein the amino group of a thioamine is covalently bonded to the carbonyl group of an α-hydroxycarboxylic acid or salicylic acid moiety, forming an amide bond therewith.

As used herein, "bis-amide" means any compound of formula IV wherein the amino groups of a diaminodisulfide are covalently bonded to the carbonyl group of an α-hydroxycarboxylic acid or salicylic acid moiety, forming amide bonds therewith.

As used herein, "cosmetic" means a formulation to be administered to the skin which improves the texture or appearance thereof, without necessarily rendering a benefit or an effect of treating or preventing an abnormal biological condition or a disease. Such improvement includes providing a temporary moisturizing effect to the epidermis of mammalian skin. A safe and effective amount of a cosmetic means an amount of the cosmetic sufficient to render a beneficial effect to the skin, but low enough to avoid side effects, such as, damaging the structure or function of the skin.

As used herein, "pharmaceutical" means a formulation to be administered to the skin which renders a benefit or an effect of treating or preventing an abnormal biological condition or a disease.

As used herein, "alkyl" means a saturated hydrocarbon. Further, the term "alkyl" as used herein includes both straight, e.g., n-propyl, n-butyl, n-pentyl, etc., and branched, e.g., isopropyl, t-butyl, isopentyl, etc., chained hydrocarbons.

As used herein, "alkenyl" means a hydrocarbon having at least one double bond.

As used herein, "alkynyl" means a hydrocarbon having at least one triple bond.

As used herein, "salicylyl" means 2-hydroxybenzoyl.

As used herein, "salicylate" means 2-hydroxybenzoate.

As used herein, "lactyl" means either d-, l- or dl-2-hydroxypropanoyl.

As used herein, "lactate" means either d-, l- or dl-2-hydroxypropanoate.

As used herein, "eq." means a molar equivalent relative to the limiting reagent in the reaction mixture.

Synthesis

The compounds of the present invention can be synthesized in accordance with standard organic chemical techniques using readily/commercially available starting materials.

Examples of the synthesis of the compounds of formula I and formula IV are described below in Scheme 1.

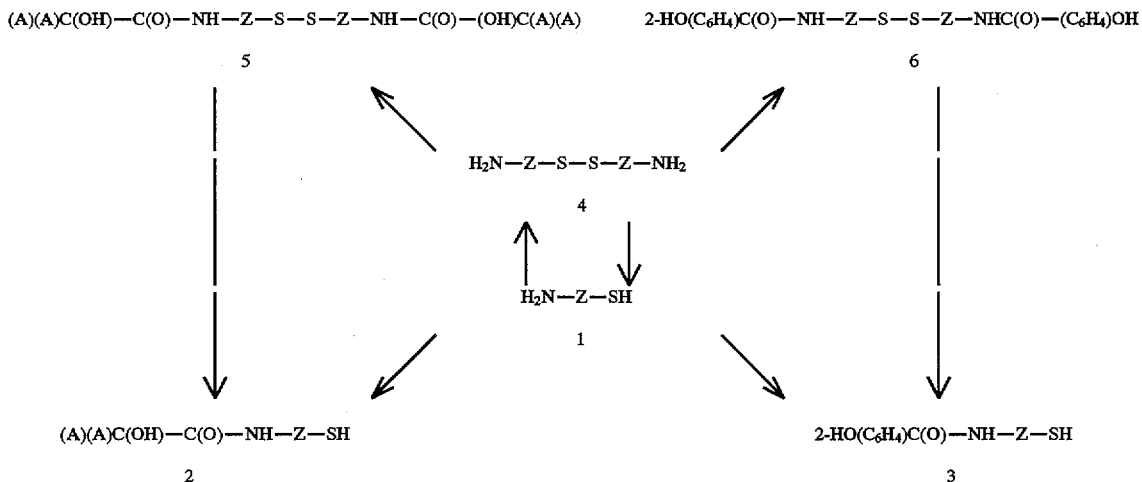

Thioamine 1, where Z is defined above, can be prepared from HO—Z—$NH_2$ and carbon disulfide, followed by hydrolysis of the cyclic intermediate (Mills Jr. et al., *J. Am. Chem. Soc.*, 62:1173 (1940)), wherein HO—Z—$NH_2$ is prepared from an ω-hydroxycarboxylic acid of the formula HO—Y—COOH, where Y is $C_3$–$C_{12}$ alkyl, $C_3$–$C_{12}$ alkenyl and $C_3$–$C_{12}$ alkynyl, by protection of the ω-hydroxyl group (T. D. Greene, *Protecting Groups in Organic Synthesis*, John Wiley & Sons, New York, 1981) followed by amidation with ammonia or its equivalent, reduction of the amide carbonyl with lithium aluminum hydride or any other reducing agent known by those of ordinary skill in the art useful for reducing lactam carbonyl groups and removal of the protecting group. Alternatively, when Z=$CH_2CH_2$, thioamine 1 can be prepared via reaction between ethyleneimine and hydrogen sulfide (Mills Jr. et al., *J. Am. Chem. Soc.*, 62:1173 (1940)) or obtained commercially as its hydrochloride salt from, for example, Aldrich Chemical Company, Inc., Milwaukee, Wis. Such hydrochloride or other acid salts of thioamine 1 can be converted to their free base form by dissolving the acid salt of 1 in a suitable organic solvent such as, for example, methylene chloride, and washing the organic solution of the acid salt of 1 with a base, preferably with an aqueous solution of a base such as an alkali metal or alkaline earth bicarbonate, carbonate or hydroxide, until the washings are of basic pH. The organic solution containing the free base form of thioamine 1 can optionally be dried and then concentrated to afford the free base form of thioamine 1.

Thioamime 1 is then amidated with either an α-hydroxycarboxylic acid of the formula (A)(A)C(OH)—$CO_2H$ or a hydroxybenzoic acid of the formula 2-(HO)$C_6H_4CO_2H$, wherein A is defined above. Optionally, thioamine 1 is amidated with a protected α-hydroxycarboxylic acid having the formula (A)(A)C(OP)—$CO_2H$ or a protected hydroxybenzoic acid of the formula 2-(PO)$C_6H_4CO_2H$, wherein A is defined as above and P is a suitable protecting group which allows the thioamine amino group to participate in an amidation reaction with the carboxyl group of either protected or unprotected carboxylic acid without interference from the unprotected hydroxyl group. It is to be understood that the (HO) moiety of 2-(HO)$C_6H_4CO_2H$ or the (PO) moiety of 2-(PO)$C_6H_4CO_2H$ is "ortho" relative to the carboxyl group. Suitable protecting groups are those which may be removed subsequent to the amidation reaction with thioamine 1 without resulting in cleavage of the newly formed amide bond. Examples of such protecting groups may be found in T. D. Greene, *Protecting Groups in Organic Synthesis*, John Wiley & Sons, New York, 1981. Where A is optionally substituted with one or more hydroxyl groups, one or more of those hydroxyl groups may be optionally protected with a suitable protecting group found in T. D. Greene, *Protecting Groups in Organic Synthesis*, John Wiley & Sons, New York, 1981.

Thioamine 1 can be heated with either the protected or unprotected carboxylic acids, optionally in the presence of an acid catalyst, to obtain amides 2 or 3, respectively. Such an amidation proceeds with concomitant loss of water. The amidation reaction can proceed in a suitable, preferably high boiling, organic solvent, or can proceed neat in the absence of solvent. Suitable acid catalysts which can be used include, but are not limited to hydrochloric acid, sulfuric acid, p-toluene sulfonic acid, methanesulfonic acid and other such acid catalysts known to those skilled in the art. Where the hydroxyl group of either (A)(A)C(OH)—$CO_2H$ or 2-(HO)$C_6H_4CO_2H$ is protected with a protecting group, the protecting group (P) should be stable to acidic conditions.

The amidation of thioamine 1 with either (A)(A)C(OH)—$CO_2H$, (A)(A)C(OP)—$CO_2H$, 2-(HO)$C_6H_4CO_2H$ or 2-(PO)$C_6H_4CO_2H$, or an alkylester derivative thereof, is preferably conducted in the presence of a reaction solvent including, but not limited to methylene chloride, chloroform, carbon tetrachloride, benzene, toluene, xylenes, tetrahydrofuran, diethyl ether, other suitable solvents known to those skilled in the art, and mixtures thereof.

Preferably, the protected or unprotected carboxylic acids are converted to their respective alkyl ester derivatives, preferably methyl ester derivatives, prior to amidation with thioamine 1 via means recited above. The alkyl esters are prepared by treating the carboxylic acids, optionally in the presence of organic solvent, with the desired alkanol, preferably methanol, followed by thionyl chloride. After esterification is complete, the resulting mixture is neutralized via the addition of base, preferably an alkali metal or alkaline earth carbonate or bicarbonate. The resulting mixture is purified via conventional means, i.e., distillation, column chromatography, recrystallization and the like, to afford the desired alkyl ester derivative. The alkyl esters can also be prepared by heating the protected or unprotected carboxylic acids in a desired alkanol, preferably methanol, in the presence of an acid catalyst recited above but in the absence of thionyl chloride. Purification via standard means such as distillation, column chromatography, or recrystallization affords the desired alkyl ester derivative.

The protected or unprotected carboxylic acids may also be converted to their acid halide derivatives, preferably acid chloride derivatives, prior to amidation with 1. The protected or unprotected carboxylic acids may be treated with either thionyl chloride or oxalyl chloride to give the corresponding acid chlorides, which may then react with 1 to give amides 2 and 3 respectively. Such an amidation is generally performed in an organic solvent including, but not limited to methylene chloride, chloroform, carbon tetrachloride, benzene, toluene, xylenes, tetrahydrofuran, diethyl ether, other aprotic organic solvents known to those skilled in the art, and mixtures thereof. The amidation of thioamine 1 with an acid chloride derivative of the carboxylic acids $(A)(A)C(OH)—CO_2H$, $(A)(A)C(OP)—CO_2H$, $2-(HO)C_6H_4CO_2H$ or $2-(PO)C_6H_4CO_2H$ is preferably performed in the presence of a base including, but not limited to triethylamine, diisopropylethylamine, pyridine, 4-dimethylaminopyridine, other bases known to those skilled in the art, and mixtures thereof. If 1 and the protected or unprotected carboxylic acids are soluble in the base, the organic solvent may optionally be omitted.

In addition, thioamine 1 may be amidated by either the protected or unprotected carboxylic acids in the presence of coupling agents such as dicyclohexylcarbodiimide. When dicyclohexylcarbodiimide is used, it may be advantageous to protect the sulfhydryl group of thioamine 1 with a protecting group described in T. W. Greene, *Protective Groups in Organic Synthesis*, John Wiley & Sons, New York, 1981. Preferably, a protected carboxylic acid having the formula $(A)(A)C(OP)—CO_2H$ or $2-(PO)C_6H_4CO_2H$ is used. Such a reaction is generally performed in an organic solvent as described above.

If either $(A)(A)C(OP)—CO_2H$ or $2-(PO)C_6H_4CO_2H$ is used to amidate 1, the protecting group (P) is removed to give amides 2 or 3, respectively. Methods for removing the protecting group can be found in T. W. Greene, *Protective Groups in Organic Synthesis*, John Wiley & Sons, New York, 1981.

Diaminodisulfide 4, a starting material for bis-amides 5 and 6, can be prepared via hydrogen peroxide oxidation of 1 (Mills Jr. et al., *J. Am. Chem. Soc.*, 62:1173 (1940)). Moreover, diaminodisulfide 4 can be converted back to 1 via reduction with $NaBH_4/AlCl_3$. For example, diaminodisulfide 4 is dissolved in a polar organic solvent, preferably diethylene glycol monomethyl ether, and treated with 5–20 eq., preferably 10–15 eq. of $NaBH_4$ and 1–5 eq., preferably 1–2 eq. of $AlCl_3$. After the reaction is complete, the reaction mixture is quenched with aqueous acid and the sulfhydryl group-containing amide product is extracted into organic solvent. The organic solvent containing the amide product is optionally dried using conventional drying agents including those described above and purified by distillation, column chromatography, recrystallization or other means known to those skilled in the art to afford thioamine 1. In this way, either 1 or 4 can serve as a starting material for amides 2 and 3 or bis-amides 5 and 6.

Diaminodisulfide 4, when $Z=CH_2CH_2$, can be obtained commercially as its hydrochloride salt from, for example, Aldrich Chemical Company, Inc., Milwaukee, Wis. Such hydrochloride or other acid salts of diaminodisulfide 4, such as for example the hydrosulfate salt of 4, can be converted to their free base form by dissolving the acid salt of 4 in a suitable organic solvent such as, for example, methylene chloride, and washing the organic solution of the acid salt of 4 with a base, preferably an alkali metal or alkaline earth bicarbonate, carbonate or hydroxide in aqueous solution, until the washings are of basic pH. The organic solution containing the free base form of diaminodisulfide 4 can be optionally dried using drying agents such as sodium sulfate, potassium carbonate and preferably magnesium sulfate, and then concentrated to afford the free base form of 4.

Diaminodisulfide 4 is then bis-amidated with either an α-hydroxycarboxylic acid of the formula $(A)(A)C(OH)—CO_2H$ or a hydroxybenzoic acid of the formula $2-(HO)C_6H_4CO_2H$, wherein A is defined above. Optionally, diaminodisulfide 4 is bis-amidated with a protected α-hydroxycarboxylic acid having the formula $(A)(A)C(OP)—CO_2H$ or a protected hydroxybenzoic acid of the formula $2-(PO)C_6H_4CO_2H$, wherein A is defined as above and P is a suitable protecting group which allows the thioamine amino group to participate in an amidation reaction with the carboxyl group of either protected or unprotected carboxylic acid without interference from the unprotected hydroxyl group. It is to be understood that the (HO) moiety of $2-(HO)C_6H_4CO_2H$ or the (PO) moiety of $2-(PO)C_6H_4CO_2H$ is "ortho" relative to the carboxyl group. Suitable protecting groups are those which may be removed subsequent to the bis-amidation reaction with diaminodisulfide 4 without resulting in cleavage of the newly formed amide bonds. Examples of such protecting groups may be found in T. D. Greene, *Protecting Groups in Organic Synthesis*, John Wiley & Sons, New York, 1981. Where A is optionally substituted with one or more hydroxyl groups, one or more of those hydroxyl groups may be optionally protected with a suitable protecting group as defined in T. D. Greene, *Protecting Groups in Organic Synthesis*, John Wiley & Sons, New York, 1981.

Diaminodisulfide 4 can be heated with either the protected or unprotected carboxylic acids, optionally in the presence of an acid catalyst, to obtain bis-amides 5 or 6, respectively. Such bis-amidation proceeds with concomitant loss of water. The bis-amidation reaction can proceed in a suitable, preferably high boiling, organic solvent, or can proceed neat in the absence of solvent. Suitable acid catalysts which can be used include, but are not limited to hydrochloric acid, sulfuric acid, p-toluene sulfonic acid, methanesulfonic acid and other such acid catalysts known to those skilled in the art. Where the hydroxyl group of either $(A)(A)C(OH)—CO_2H$ or $2-(HO)C_6H_4CO_2H$ is protected with a protecting group, the protecting group (P) should be stable to acidic conditions. The bis-amidation of diaminodisulfide 4 with either $(A)(A)C(OH)—CO_2H$, $(A)(A)C(OP)—CO_2H$, $2-(HO)C_6H_4CO_2H$ or $2-(PO)C_6H_4CO_2H$, or an alkylester derivative thereof, is preferably conducted in the presence of a reaction solvent including, but not limited to methylene chloride, chloroform, carbon tetrachloride, benzene, toluene, xylenes, tetrahydrofuran, diethyl ether, other suitable solvents known to those skilled in the art, and mixtures thereof.

Preferably, the protected or unprotected carboxylic acids are converted to their respective alkyl ester derivatives, preferably methyl ester derivatives, prior to bis-amidation with diaminodisulfide 4 via means recited above. The alkyl esters are prepared by treating the carboxylic acids, optionally in the presence of organic solvent, with the desired alkanol, preferably methanol, followed by thionyl chloride. After esterification is complete, the resulting mixture is neutralized via the addition of base, preferably an alkali metal or alkaline earth carbonate or bicarbonate. The resulting mixture is purified via conventional means, i.e., distillation, column chromatography, recrystallization or the like, to afford the desired alkyl ester derivative. The alkyl esters can also be prepared by heating the protected or unprotected carboxylic acids in a desired alkanol, preferably methanol, in the presence of an acid catalyst recited above but in the absence of thionyl chloride. Purification via standard means such as distillation, column chromatography, or recrystallization affords the desired alkyl ester derivative.

The protected or unprotected carboxylic acids may also be converted to their acid halide derivatives, preferably acid chloride derivatives, prior to bis-amidation with 4. The protected or unprotected carboxylic acids may be treated with either thionyl chloride or oxalyl chloride to give the corresponding acid chlorides, which may then react with 4 to give bis-amides 5 and 6 respectively. Such bis-amidation is generally performed in an organic solvent including, but not limited to methylene chloride, chloroform, carbon tetrachloride, benzene, toluene, xylenes, tetrahydrofuran, diethyl ether, other aprotic organic solvents known to those skilled in the art, and mixtures thereof. The bis-amidation of diaminodisulfide 4 with an acid chloride derivative of the carboxylic acids (A)(A)C(OH)—$CO_2H$, (A)(A)C(OP)—$CO_2H$, 2-(HO)$C_6H_4CO_2H$ or 2-(PO)$C_6H_4CO_2H$ is preferably performed in the presence of a base including, but not limited to triethylamine, diisopropylethylamine, pyridine, 4-dimethylaminopyridine, other bases known to those skilled in the art, and mixtures thereof. If 4 and the protected or unprotected carboxylic acids are soluble in the base, the organic solvent may optionally be omitted.

In addition, diaminodisulfide 4 may be bis-amidated by either the protected or unprotected carboxylic acids in the presence of dicyclohexylcarbodiimide. When dicyclohexylcarbodiimide is used it may be advantageous to protect the sulfhydryl groups of diaminodisulfide 4 with a protecting group described in T. W. Greene, *Protective Groups in Organic Synthesis*, John Wiley & Sons, New York, 1981. Preferably, a protected carboxylic acid is used. Such a reaction is generally performed in an organic solvent as described above.

If either (A)(A)C(OP)—$CO_2H$ or 2-(PO)$C_6H_4CO_2H$ is used to bis-amidate 4, the protecting group (P) is removed to give bis-amides 5 or 6, respectively. Methods for removing the protecting group can be found in T. W. Greene, *Protective Groups in Organic Synthesis*, John Wiley & Sons, New York, 1981.

In a further embodiment of the invention, bis-amides 5 and 6 can be prepared in a step-wise fashion such that the α-hydroxycarboxylic or salicylic acid moiety on each terminus of bis-amides 5 or 6 is different. For example, a thioamine 1 can be oxidatively coupled, using hydrogen peroxide (Mills Jr. et al., *J. Am. Chem. Soc.*, 62:1173 (1940)) to a second thioamine which is N-protected with a protecting group stable to hydrogen peroxide. It is well within the purview of one of ordinary skill in the art to select such a protecting group. The resulting diaminodisulfide 4 bears an N-protected amino group at one terminus of the molecule and an unprotected amino group at the other terminus. The resulting mono-protected diaminodisulfide is then amidated with an optionally protected first α-hydroxy or salicylic acid or derivative thereof using any of the methods described above. The protecting group is then removed from the amide adduct using conditions which will not hydrolyze or otherwise cleave the newly-formed amide bond, thereby exposing a free amino group available for a second amidation. The free amino group is then amidated with an optionally protected second α-hydroxy or salicylic acid or derivative thereof, which is the same or different from the optionally protected first α-hydroxy or salicylic acid or derivative thereof, using any of the methods described above. By this method, unsymmetrical bis-amides derived ultimately from thioamine 1, having different α-hydroxy or salicylic acid groups on each terminus, can be obtained.

Furthermore, bis-amides 5 and 6 can be directly converted to amides 2 and 3, respectively, via treatment with $NaBH_4$/$AlCl_3$. The desired bis-amide is dissolved in a polar organic solvent, preferably diethylene glycol monomethyl ether, and treated with 5–20 eq., preferably 10–15 eq. of $NaBH_4$ and 1–5 eq., preferably 1–2 eq. of $AlCl_3$. After the reaction is complete, the reaction mixture is quenched with aqueous acid and the amide product is extracted into organic solvent. The organic solvent containing the amide product is optionally dried using conventional drying agents including those described above and purified by distillation, column chromatography, recrystallization or other means known to those skilled in the art to afford amides 2 or 3.

If a heterogeneous mixture of amides is desired, an unsymmetrical bis-amide is first prepared from diaminodisulfide 4, as described above. The resulting unsymmetrical bis-amide is then treated with $NaBH_4$/$AlCl_3$, as described above, so as to cleave the disulfide bond thereof and afford a 1:1 mixture of different thioamides.

It is to be understood that in addition to using the synthetic methods described hereinabove to obtain starting materials for the amides and bis-amides of the present invention, starting materials such as alkyl esters of α-hydroxycarboxylic acids and salicylic acid can be obtained commercially. For example, methyl salicylate and the d- and l-enantiomers of methyl lactate can be obtained from Aldrich Chemical Co., Milwaukee, Wis.

Compositions

The compositions of the present invention can be used to treat skin atrophy and other disorders including but not limited to dry skin, severe dry skin, dandruff, acne, keratoses, psoriasis, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers.

In treating or preventing an abnormal biological condition or a disease such as skin atrophy or any other skin disorder described above, pharmaceutical compositions containing about 0.005 to about 50 wt. %, preferably 0.01 to about 25 wt. % and most preferably 0.01 to about 5 wt. % of the amide of formula I or bis-amide of formula IV can be employed.

In improving the texture or appearance of the skin, topical cosmetic compositions containing 0,005 to about 50 wt. %, preferably 0.005 to about 1 wt. % and most preferably 0.005 to about 0.5 wt. % of the amide of formula I or bis-amide of formula IV can be employed.

It should be understood that two or more amides or bis-amides of the present invention can be used in combination such that the combined weight % of those amides or bis-amides used in the above-mentioned compositions is within those ranges mentioned above. Such compositions are preferably to be administered topically, so as to minimize systemic effects or undesirable side effects.

The novel compounds may also be employed in pharmaceutical compositions suitable for parenteral (including subcutaneous, transdermal, intramuscular and intravenous) administration, although the most suitable route in any case will depend on the nature and severity of the condition being treated. The most preferred mode of administration for treating skin disorders, in particular skin atrophy or the skin disorders described above, is topical.

In addition, the amides and bis-amides of the present invention may be further employed in cosmetic compositions. In such an instance, the preferred mode of administration for improving the texture or appearance of the skin is topical.

The amides and bis-amides of the present invention can be formulated into suitable cosmetic or pharmaceutical compositions depending on the particular use for which it is to be intended, for example, cosmetic or therapeutic. The pharmaceutical and cosmetic compositions can comprise one or more of the amides of formula I or bis-amides of formula IV and a pharmaceutically or cosmetically acceptable carrier or excipient. Examples of such pharmaceutically acceptable carriers or excipients are well known to those skilled in the art and can be found, for example, in *Remington's Pharmaceutical Sciences,* Eighteenth Edition, A. R. Gennaro, Ed., Mack Publishing Co., Easton, Pa., 1990. Examples of such cosmetically acceptable carriers or excipients are well known to those skilled in the art and can also be found, for example, in *CTFA International Cosmetic Ingredient Dictionary,* Fourth Edition, J. M. Nikitakis, Ed., The Cosmetic, Toiletry, and Fragrance Association, Washington, D.C., 1991.

The pharmaceutical and cosmetic compositions of the present invention intended for topical application may contain carrier, excipient or vehicle ingredients such as, for example, water, acetone, ethanol, ethylene glycol, propylene glycol, butane-1,3-diol, isopropyl myristate, isopropyl palmitate, mineral oil, and mixtures thereof to form lotions, tinctures, creams, emulsions, mousses, sprays, foams, powders, gels or ointments which are non-toxic and pharmaceutically or dermatologically acceptable. Additionally, moisturizers or humectants can be added to the present compositions if desired. Examples of such additional ingredients useful for pharmaceutical compositions can be found in *Remington's Pharmaceutical Sciences,* Eighteenth Edition, A. R. Gennaro, Ed., Mack Publishing Co., Easton, Pa., 1990. Examples of such additional ingredients useful for cosmetic compositions can be found in *CTFA International Cosmetic Ingredient Dictionary,* Fourth Edition, J. M. Nikitakis, Ed., The Cosmetic, Toiletry, and Fragrance Association, Washington, D.C., 1991.

In addition to these and other vehicles which will be obvious to those of ordinary skill in the art, it will be understood that the pharmaceutical and cosmetic compositions of the present invention may include other ingredients such as those that improve or eradicate age spots, keratoses and wrinkles; pigments; analgesics; anesthetics; antiacne agents; antibacterials; antiyeast agents; antifungal agents; antiviral agents; antidandruff agents; antidermatitis agents; antipruritic agents; antiemetics; antimotion sickness agents; antiinflammatory agents; antihyperkeratolytic agents; antidryskin agents; antiperspirants; antipsoriatic agents; antiseborrheic agents; hair conditioners and hair treatment agents; antiaging agents; antiwrinkle agents; antiasthmatic agents and bronchodilators; sunscreen agents; antihistamine agents; skin lightening agents; depigmenting agents; vitamins; corticosteroids; tanning agents; hormones; retinoids; topical cardiovascular agents; clotrimazole; ketoconazole; miconazole; griseofulvin; hydroxyzine; diphenhydramine; pramoxine; lidocaine; procaine; mepivacaine; monobenzone; erythidocaine; procaine; mepivacaine; monobenzone; erythromycin; tetracycline; clindamycin; meclocyline; hydroquinone; minocycline; naproxen; ibuprofen; theophylline; cromolyn; albuterol; retinoic acid; 13-cis retinoic acid; hydrocortisone; hydrocortisone 21-acetate; hydrocortisone 17-valerate; hydrocortisone 17-butyrate; betamethasone valerate; betamethasone dipropionate; triamcinolone acetonide; fluocinonide; clobetasol propionate; benzoyl peroxide; crotamiton; propranolol; promethazine; vitamin A palmitate; vitamin E acetate and mixtures thereof. Concentrations of these ingredients will vary depending upon intended use, i.e., therapeutic or cosmetic.

Moreover, it will be understood that the pharmaceutical and cosmetic compositions of the present invention can additionally include one or more hydroxyacids, which are well known to the skilled artisan as described above, present in an effective amount to improve the appearance or the texture of the skin. The hydroxyacid(s) can be present in an amount ranging from about 0.5 to about 15% by weight. A preferred composition is a cosmetic composition, in which the total amount of hydroxyacid(s) is preferably from about 0.5 to about 5%, more preferably from about 0.5 to about 3%, and most preferably from about 0.75% to about 2%. For the purposes of the present invention, the term "hydroxyacid," "hydroxyacids" or "hydroxyacid(s)" includes both alpha- and beta-hydroxyacids in their free acid form, as well as covalent derivatives thereof. Suitable hydroxyacids include, but are not limited to, alpha-hydroxyacids such as lactic acid, glycolic acid, citric acid, alpha-hydroxyoctanoic acid, alpha-hydroxydecanoic acid, alpha-hydroxylauric acid, tartaric acid, glucouronic acid, galactouronic acid, alpha-hydroxybutyric acid, alpha-hydroxyisobutyric acid, malic acid, mandelic acid, pyruvic acid, and tartronic acid, preferably alpha-hydroxydecanoic and alpha-hydroxyoctanoic acids; and beta-hydroxy acids such as salicylic acid. Suitable covalent derivatives include esters, thioesters, amides and lactones, and mixtures thereof. In a preferred embodiment, the composition comprises a mixture of free hydroxyacids, such as alpha-hydroxydecanoic, alpha-hydroxyoctanoic and salicylic acids.

The amides and bis-amides of the present invention can be used as their pharmaceutically or cosmetically acceptable salts. Such salts include, but are not limited to, hydrochloride, hydrobromide, hydroiodide, acetate, citrate, tartrate, malate, ammonium, alkylammonium salts and the like, as well as salts of one or more alpha- or beta-hydroxyacids described above.

It is to be understood that the amides of formula I and bis-amides of formula IV can exist as a single, i.e., d- or l-enantiomer, or a racemic mixture thereof, as well as mixtures of diastereomers. The instant invention encompasses optical isomers of the compounds disclosed herein. Standard techniques for purification of enantiomers can be found in, for example, *Stereochemistry of Carbon Compounds* by E. L. Eliel (McGraw Hill, 1962) and *Tables of Resolving Agents* by S. H. Wilen (University of Notre Dame Press, 1972).

Methods for Treating or Preventing an Abnormal Skin Condition or Disease

The present invention relates to a method for treating or preventing an abnormal skin condition or disease such as skin atrophy or other skin disorders including but not limited to dry skin, severe dry skin, dandruff, ache, keratoses, psoriasis, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers. Such a method comprises administering to the skin a safe and effective amount of one or more of the amides or bis-amides of the present invention. While the present invention relates to amides of formula I and bis-amides of formula IV used to treat skin disorders, the present invention further relates to the use of compositions, such as those discussed above, comprising one or more of the amides or bis-amides of the present invention, to be used for treating skin disorders. The amount of amide or bis-amide and frequency of treatment will vary widely depending upon the extent of skin disease or condition already in existence in the subject (if such exists), the rate of progression of skin disease or condition, and the extent of treatment desired.

A preferred method of treating the skin is via chronic topical application of a safe and effective amount of the amide or bis-amide to regulate skin atrophy to treat or prevent the abnormal skin condition or disease. The amount of amide or bis-amide and frequency of topical application to the skin can vary widely, depending upon the particular skin disorder and the severity thereof. It is well within the purview of the skilled artisan, such as a dermatologist or other health care provider, to regulate dosages according to patient needs. It is suggested as an example that topical application range from about once per week to about 4 or 5 times daily, preferably from about 3 times a week to about 3 times daily, most preferably about once or twice per day. The composition for topical application will comprise from about 0.005% to about 50%, preferably from about 0.01% to about 25%, most preferably from about 0.01% to about 5% of the active compound or mixture of compounds. By "chronic" application, it is meant herein that the period of topical application may be over the lifetime of the patient, preferably for a period of at least about one month, more preferably from about three months to about twenty years, more preferably from about six months to about ten years, more preferably still from about one year to about five years, thereby resulting in the treatment or prevention of the abnormal skin condition or disease described.

In another embodiment of the invention, treating or preventing an abnormal skin condition or disease involves administering both a safe and effective amount of the amide or bis-amide(s) and a safe and effective amount of one or more of a sunscreening agent, an anti-inflammatory agent, an anti-oxidant/radical scavenging agent, a chelating agent, a retinoid and/or a benzofuran derivative to the skin simultaneously. As used herein, "simultaneous application" or "simultaneously" means administering the agents to the skin at the same situs on the body at about the same time. Though this can be accomplished by administering the agents separately to the skin, preferably a composition comprising all the desired agents commingled is administered to the skin. The amount of sunscreening agent administered is generally from about 0.02 mg to about 1.0 mg per $cm^2$ skin. The amount of anti-inflammatory agent administered is generally from about 0.005 mg to about 0.5 mg, preferably from about 0.01 mg to about 0.1 mg per $cm^2$ skin. The amount of chelating agent generally administered is from about 0.001 mg to about 1.0 mg, preferably from about 0.01 mg to about 0.5 mg, more preferably from about 0.05 mg to about 0.1 mg per $cm^2$ skin. The amount of retinoid administered is generally from about 0.00001 mg to about 0.02 mg per $cm^1$ skin. The amount of benzofuran derivative administered is generally from about 0.001 mg to about 1.0 $mg/cm^2$ skin per application, preferably from about 0.01 to about 0.5 $mg/cm^2$ skin per application. The amount of amide or bis-amide(s) administered is generally from about 0.001 mg to about 1.0 mg per $cm^2$ skin per application, preferably from about 0.01 mg to about 0.5 mg per $cm^2$, more preferably from about 0.05 to about 0.25 $mg/cm^2$ skin per application, which may vary upon the severity of the condition to be treated and the efficacy of the compounds employed.

Methods for Improving the Texture or Appearance of the Skin

The present invention also relates to a method for improving the texture or appearance of the skin. Improving the texture or appearance of the skin is meant to encompass enhancing the skin's natural look and/or feel so as to increase the beauty and/or smoothness of the skin from its pre-treated state, or to mask unwanted symptoms of an abnormal biological condition or a disease. Such cosmetic uses include but are not limited to moisturizing skin; masking skin blemishes or other undesired attributes; highlighting the skin as, for example, an eye shadow; improving skin texture; and the like. Such abnormal biological conditions or diseases include, but are not limited to dry skin, severe dry skin, dandruff, acne, keratoses, psoriasis, eczema, skin flakiness, pruritus, age spots, lentigines, melasmas, wrinkles (both coarse and fine, caused by intrinsic as well as extrinsic damage), warts, blemished skin, hyperpigmented skin, hyperkeratotic skin, inflammatory dermatoses, age-related skin changes and skin in need of cleansers, as well as the effects of skin atrophy. Such a method comprises administering to the skin a safe and effective amount of one or more of the amides or bis-amides of the present invention. The amount of amide or bis-amide and frequency of topical application to the skin can vary widely, depending upon desirability of use by the skilled artisan, e.g., a user of cosmetics.

While the present invention relates to amides of formula I and bis-amides of formula IV used to treat skin disorders, the present invention further relates to the use of compositions, such as those discussed above, comprising one or more of the amides or bis-amides of the present invention, to be used for treating skin disorders.

A preferred method of treating the skin is via occasional topical application of a safe and effective amount of the amide or bis-amide to improve the texture or appearance of the skin. The amount of amide or bis-amide and frequency of treatment will vary widely depending upon the desired level of improvement of the appearance or texture of the skin and/or the extent of an abnormal skin condition or disease, if one such exists, desired to be masked. It is suggested as an example that topical application range from about once per week to about 4 or 5 times daily, preferably from about 3 times a week to about 3 times daily, most preferably about once or twice per day. The composition for topical application will comprise from about 0.005 to about 50 wt. %, preferably 0.005 to about 1 wt. % and most preferably 0.005 to about 0.5 wt. % of the amide of formula I or bis-amide of formula IV. By "occasional" application, it is meant herein that the period of topical application may be as often as desired and/or needed to improve the texture or appearance of the skin.

Cosmetic uses encompassed by the cosmetic compositions of the present invention include but are not limited to moisturizing skin; masking skin blemishes or other undesired attributes; highlighting the skin as, for example, an eye shadow; improving skin texture; and the like. The amount of amide or bis-amide and frequency of topical application to the skin can vary widely, depending upon desirability of use.

In another embodiment of the invention, improving the texture or appearance of the skin involves administering both a safe and effective amount of the amide or bis-amide (s) and optionally, one or more of a sunscreening agent, an anti-inflammatory agent, an anti-oxidant/radical scavenging agent, a chelating agent, a retinoid and/or a benzofuran derivative to the skin simultaneously. As used herein, "simultaneous application" or "simultaneously" means administering the agents to the skin at the same situs on the body at about the same time. Though this can be accomplished by administering the agents separately to the skin, preferably a composition comprising all the desired agents commingled is administered to the skin. If present, the amount of sunscreening agent administered is generally from about 0.02 mg to about 1.0 mg per cm$^2$ skin; the amount of anti-inflammatory agent administered is generally from about 0.005 mg to about 0.5 mg, preferably from about 0.01 mg to about 0.1 mg per cm$^2$ skin; the amount of chelating agent generally administered is from about 0.001 mg to about 1.0 mg, preferably from about 0.01 mg to about 0.5 mg, more preferably from about 0.05 mg to about 0.1 mg per cm$^2$ skin; the amount of retinoid administered is generally from about 0.00001 mg to about 0.02 mg per cm$^2$ skin; and the amount of benzofuran derivative administered is generally from about 0.001 mg to about 1.0 mg/cm$^2$ skin per application, preferably from about 0.01 to about 0.5 mg/cm$^2$ skin per application. The amount of amide or bis-amide(s) administered is generally from about 0.001 mg to about 1.0 mg per cm$^2$ skin per application, preferably from about 0.001 mg to about 0.1 mg per cm$^2$, more preferably from about 0.001 to about 0.05 mg/cm$^2$ skin per application.

The following specific, non-limiting examples concern the synthesis of the amides and bis-amides of the instant invention and the preparation of a topical lotion, topical cream, topical ointment and topical gel using vehicles previously used in other preparations. The formulations for these preparations are given below in Table 3.

EXAMPLE 1

Methyl 2-Hydroxydecanoate

A 22 L 3-neck reaction flask equipped with a cooling bath, an overhead stirrer, a thermocouple and a 1 L addition funnel was charged with 4.70 kg of 2-hydroxydecanoic acid and 16 L of methanol. A drying tube was attached to the reaction flask and the addition funnel was charged with 1 L of thionyl chloride. With efficient stirring, the contents of the reaction flask were chilled to between 0° and +5° C. and the addition of thionyl chloride was commenced. The rate of thionyl chloride addition was adjusted such that with continued cooling, the temperature of the reaction flask remained between 0° and +5° C. Under these conditions, the 1 L of thionyl chloride, as well as an additional 1 L of thionyl chloride, was completed in <2 hours. It is important to note that if the temperature of the reaction flask is allowed to fall much below 0° C., the reaction mixture will solidify, causing the stirrer to seize. If this happens, the addition of thionyl chloride must be halted, and the entire reaction mixture allowed to warm to room temperature to effect redissolution. With efficient stirring, the reaction mixture can once again be chilled to between 0° and +5° C. and the addition of thionyl chloride be completed.

Following the addition of thionyl chloride, the resulting reaction mixture was allowed to warm to room temperature overnight, with continuous stirring. The resulting solution was poured into a 100 L polypot equipped with a Lightening stirrer. Approximately 10 L of hexane was then added. With vigorous stirring, solid NaHCO$_3$, in approximately 500 g portions, was added until the vigorous evolution of gases subsided. A 5% aqueous solution of NaHCO$_3$ was gradually added until the resulting vigorous evolution of gases subsided. The resulting mixture was allowed to stir for an additional 15 minutes before siphoning off the hexane layer. The residual aqueous layer was extracted a second time with an additional 10 L portion of hexane. The hexane extracts were combined, dried over Na$_2$S$_4$ and concentrated in vacuo to afford 5.05 kg (93%) of the title compound as a pale, yellow liquid, purity 98% by gas-liquid partition chromatography: IR exhibited v(OH), v(C=O) and v(C—O) bands consistent with the structure of the title compound.

EXAMPLE 2

N,N'-Bis(2-hydroxydecanoyl)cystamine

A 15 L polypot was charged with 1.5 kg cystamine H$_2$SO$_4$ and 2 L of methylene chloride. With vigorous stirring, an aqueous solution of 40% NaOH was added to the resulting suspension and the resulting biphasic mixture was allowed to stir for an additional 15 minutes. The organic layer was separated from the aqueous layer with the aid of a siphon and the entire extraction process was repeated 2 additional times. Combined organic extracts were dried (MgSO$_4$) and concentrated in vacuo to yield 390 g (2.56 mole; 48% yield) of cystamine free-base.

The resulting cystamine free-base was treated with 4 L of toluene, and the resulting mixture was transferred to a 12 L 3-neck flask equipped with an overhead stirrer, heating mantle and reflux condenser. The 12 L 3-neck flask containing the mixture of cystamine free-base and toluene was charged with 1.60 kg of methyl 2-hydroxydeoanoate obtained from Example 1 and the resulting mixture was heated at reflux for 1 hour. At this point, the reflux condenser was turned from a vertical to a nearly horizontal position so as to allow distillation to occur. Over a 1–2 hour period, approximately 1400 mL of distillant was collected. The distillant was biphasic and consisted mostly of toluene in the lower layer and methanol in the upper layer. The reflux condenser was returned to its vertical reflux position and the reaction mixture was heated under a gentle reflux and with vigorous stirring for an additional 6 hours during which time a heavy precipitate formed. Upon cooling to room temperature, the entire contents of the reaction vessel solidified. 5 L of toluene were added and the resulting mixture was allowed to stir until a homogeneous suspension of solid material was obtained. The suspended solid was collected by vacuum filtration, washed with 4–5 L of toluene, then with 4–5 L of ethyl acetate before being pressed dry.

The resulting crude product was dissolved in approximately 30 L of near boiling γ-butyrolactone and the resulting solution was allowed to cool and stand overnight at 20° C. The resulting white, crystalline precipitate was collected by vacuum filtration, washed with 2–3 L of fresh γ-butyrolactone, 5 L of ethyl acetate and finally 5 L of hexane before drying in a forced air oven at 60° C. to afford 1.219 kg (96%) of the title compound: mp.=180°–183° C.; IR exhibited combined v(OH) and v(NH) bands, a distinct Amide I and an Amide II band consistent with the structure of the title compound.

EXAMPLE 3

Methyl 2-Hydroxyoctanoate

Methyl 2-hydroxyoctanoate was obtained following the procedure of Example 1, except that 2-hydroxyoctanoic acid was used in place of 2-hydroxydecanoic acid.

EXAMPLE 4

N,N'-Bis(2-hydroxyoctanoyl)cystamine, N,N'-Bis(2-hydroxydodecanoyl)cystamine, N,N'-Bis(lactyl)cystamine and N,N'-Bis(salicylyl)cystamine N,N'-Bis(2-hydroxyoctanoyl)cystamine, N,N'-Bis(2-hydroxydodecanoyl)cystamine, N,N'-Bis(lactyl)cystamine and N,N'-Bis(salicylyl)cystamine were obtained following the procedure of Example 2, except that methyl 2-hydroxyoctanoate, methyl 2-hydroxydodecanoate, methyl lactate and methyl salicylate, respectively, were used in place of methyl 2-hydroxydecanoate.

EXAMPLE 5

N-(2-Hydroxyoctanoyl)cysteamine

To a 1 L 1-neck round bottom reaction flask equipped with a teflon-coated stirrer bar and a reflux condenser was added 600 mL of diethylene glycol monomethyl ether followed by 18.0 g of N,N'-Bis(2-hydroxyoctanoyl)cystamine obtained from Example 4, 60.0 g of $NaBH_4$ and 11.0 g of $AlCl_3$. The resulting mixture was allowed to stir at room temperature overnight. The reaction flask was placed in an ice bath and to the reaction flask was gradually added, with vigorous stirring, 6M HCl until the vigorous evolution of gases ceased. Following the addition of the 6M HCl, the pH of the resulting aqueous phase was <3. The resulting mixture was extracted with three 700 mL portions of ethyl acetate. The ethyl acetate washings were combined, back-extracted with three 700 mL portions of brine and three 700 mL portions of water, dried over $Na_2SO_4$, and concentrated under reduced pressure (40° C. @ 100mm Hg). The resulting semi-solid residue was triturated with hexane, and the resulting white solid was collected by vacuum filtration. The white solid was washed with 25 mL of cold hexane and air dried. The hexane mother liquor mixture was chilled to −78° C. and filtered to provide additional solid which was added to the purified white solid, above, to afford the title compound in 68% combined yield: mp.=83°–84° C.; IR ν(S—H) @2574 $cm^{-1}$ (weak); TLC $R_f$=0.6 (5% $MeOH/CH_2C_{12}$), ($R_f$ of N,N'-Bis(2-hydroxyoctanoyl)cystamine=0.5). The title compound, a microcrystalline white solid, was readily soluble in diethyl ether, ethyl acetate, ethanol and methanol, but was insoluble in either water or cold hexane.

EXAMPLE 6

N-(2-Hydroxydecanoyl)cysteamine, N-(2-hydroxydodecanoyl)cysteamine, N-(lactyl)cysteamine and N-(salicylyl)cysteamine N-(2-Hydroxydecanoyl)cysteamine, N-(2-hydroxydodecanoyl)cysteamine, N-(lactyl)cysteamine and N-(salicylyl)cysteamine were obtained following the procedure of Example 5, except that N,N'-bis(2-hydroxydecanoyl)cystamine, N,N'-bis(2-hydroxydodecanoyl)cystamine, N,N'-bis(lactyl)cystamine and N,N'-bis(salicylyl)cystamine, respectively, were used in place of N,N'-bis(2-hydroxyoctanoyl)cystamine.

EXAMPLE 7

Decrease in Skin Flakiness as Measured by Skin Desguamation

Forty female subjects with dry hands were qualified for the study based on D-squame evaluation. In this test, cellophane tape was used to remove stratum corneocytes from the skin's outer surface. The subjects did not use moisturizers or any treatment formulation on their hands on the day of testing and their baseline D-squame samples were collected. The subjects were randomly assigned to one of four treatment groups, with ten subjects per group, and were given the test formulation to take home and self-administer on the right hand only, twice a day in the morning after washing and in the evening at least 15 minutes before bedtime for four weeks. The left hand served as the untreated control site. The subjects were allowed to use the test formulation only and specifically log its use in a daily diary provided. At the end of two and four weeks, the subjects returned for testing without administering the test formulation for at least 12 hours, and were reevaluated under the same conditions.

Four D-squame discs were firmly and evenly pressed on each hand with a hand held uniform pressure device and removed by gently pulling away from the skin. The D-squame discs were mounted on clear microscope slides and labeled according to panelist name and visit. Desquamation was evaluated from the D-squame discs via an image analyzer, which was used to quantify the amount of stratum corneocytes which adhered to each disk. Skin evaluation, i.e., degree of desquamation, was carried out before treatment, and after two and four weeks of treatment.

An Optima image analyzer was used to evaluate skin flakiness. The D-squame samples containing stratum corneocytes were placed under a camera mounted on top of a light table and each image was imported to the image analyzer. The average Gray Value corresponding to the sample density was measured. The denser the sample, the higher the Gray Value difference, i.e., the higher the degree of desquamation and skin flakiness.

The test formulations and group assignments were as follows:

Group I: Formulation A

Group II: Formulation A less alphamix and less biolac, but with an additional 10% by weight Octyldodecanol/Silica Mixture Group III: Formulation A less alphamix and less biolac but with an additional 2% by weight N,N'-Bis(salicylyl)cystamine Group IV: Formulation A less alphamix and less biolac but with an additional 10% by weight N,N'-Bis(lactyl)cystamine as a 10% aqueous solution

| Formulation A | |
| --- | --- |
| Component | Percent |
| Deionized Water | 66.35 |
| Phenoxyethanol | 0.063 |
| Methyl Paraben | 0.018 |
| Imidazolidinyl Urea | 0.300 |
| Sodiim Hyaluronate | 0.090 |
| Water/Guanine/Isopropyl Alcohol/ Methylcellulose Mixture | 1.000 |
| Alphamix[1] | 2.000 |
| Biolac[2] | 2.000 |
| Tetrahydroxypropyl Ethylenediamine | 0.500 |
| Polysorbate 40 | 2.500 |
| Silicone 200[3] | 2.500 |

-continued

Formulation A

| Component | Percent |
| --- | --- |
| Polyacrylamide/$C_{13}$-$C_{14}$ Isoparaffin/Laureth-7 Mixture | 5.000 |
| Fragrance | 0.075 |
| FD&C Yellow No. 5 (1% aq. solution) | 0.026 |
| FD&C Yellow No. 6 (1% aq. solution) | 0.052 |
| FD&C Red No. 40 (0.5% aq. solution) | 0.026 |
| Cyclomethicone | 15.00 |

[1] 35% α-hydroxydecanoic acid 3.8% α-hydroxyoctanoic acid 61.2% butylene glycol
Biolac consists of 28–35% lactic acid and 65–72% inert ingredients.
[2] Dimethicone As shown below in Table 1, the results indicate that following two and four weeks of treatment, skin flakiness decreased by 17% and 38%, respectively, among Group IV subjects, i.e., those who administered a formulation comprising N,N'-bis(lactyl)cystamine. In addition, skin flakiness decreased by 16% and 27%, respectively, among Group III subjects, i.e., those who administered a formulation comprising N,N'-bis(salicylyl)cystamine. These results are clearly superior to those obtained by Group I and Group II subjects, i.e., those who administered formulations that did not comprise an amide or bis-amide of the present invention. Thus, the results shown in Table 1 clearly show that illustrative bis-amides of the present invention are useful for treating an abnormal condition of the skin.

TABLE 1

| | % Decrease in Skin Flakiness | |
| --- | --- | --- |
| | 2 Weeks | 4 Weeks |
| Group I | | |
| treated arm | −21.08 | −36.09 |
| untreated arm (control) | −43.72 | −63.21 |
| treated - untreated | 22.64 | 27.12 |
| Group II | | |
| treated arm | −8.74 | −29.30 |
| untreated arm (control) | −16.74 | −36.97 |
| treated - untreated | 8.00 | 7.67 |
| Group III | | |
| treated arm | −1.69 | 40.10 |
| untreated arm (control) | −17.96 | 13.38 |
| treated - untreated | 16.27 | 26.72 |
| Group IV | | |
| treated arm | 4.13 | 53.25 |
| untreated arm (control) | −13.23 | 14.77 |
| treated - untreated | 17.36 | 38.48 |

EXAMPLE 8

Decrease in Skin Flakiness Following the Application of a Formulation Containing 1% N-(lactyl)cysteamine Compared to Other Test Formulations Following the protocol described in Example 7, above, skin flakiness was assessed from subjects who administered various test formulations, shown below in Table 2, over a two and four week period. As can be seen from Table 2, after 2 weeks of administration, the test formulation comprising 1% N-(lactyl)cysteamine resulted in a 34.9% decrease in skin flakiness, the largest decrease in skin flakiness among all the formulations tested over 2 weeks. Thus, the results shown in Table 2 clearly demonstrate the utility of the amides of the present invention.

TABLE 2

| | % Decrease in Skin Flakiness | |
| --- | --- | --- |
| | 2 Weeks | 4 Weeks |
| 1% N-(lactyl)cysteamine | 34.9 | 21.1 |
| Formulation A | 23.0 | 29.0 |
| Formulation A | 31.4 | 30.6 |
| Formulation A | 32.8 | 36.6 |
| Formulation A (seasonal variation) | 13.5 | 25.0 |
| 0.5% dihydroxysebacic acid | 9.6 | 24.3 |
| 1.4% α-hydroxylauric acid (pH 4.04) | 27.6 | 28.7 |
| 5.28% Phytic acid | 35.6 | 19.9 |
| 1% Mandelic acid | 38.2 | 21.4 |
| 1% Ceramide 6b C10[1] plus 0.1% Ceramide 6c C8[2] | 33.7 | 24.0 |
| 0.8% Salicylic acid (47.1, 1 week) 10% Salisomes[3] | 21.0 | n/a |
| pH 3.89 | 18.0 | 26.4 |
| pH 7.0 | −1.5 | 7.6 |

[1] N-(2-hydroxydecanoyl)phytosphingosine
[2] N-(2-hydroxyoctanoyl)phytosphingosine liposomes containing salicylic acid (see EP 616 799)

EXAMPLES 9–12

Pharmaceutical or Cosmetic Compositions

EXAMPLE 9

Butylene glycol and water are mixed and dissolved in alcohol. The resultant vehicle mixture and a compound of formula I or formula IV, or a mixture thereof are mixed and dissolved. The resultant formulation is a tincture.

EXAMPLE 10

In this example a topical cream is prepared by first mixing and melting squalane, stearyl alcohol NF, cetyl alcohol polyethylene glycol cetyl ether, mineral oil NF and petrolatum USP, at 70° C. A second mixture is formed by mixing and dissolving methyl paraben NF and propyl paraben NF in water, at 70° C. The second mixture is slowly added to and mixed with the first mixture to form an emulsion. A compound of formula I or formula IV, or a mixture thereof is dispersed in the resultant emulsion at 50° C. The resultant composition is slowly cooled with mixing until the composition reaches room temperatures.

EXAMPLE 11

In this example a topical ointment is prepared. As a first step, glyceryl monostearate is mixed and melted in petrolatum USP at 70° C. As a second step, A compound of formula I or formula IV, or a mixture thereof is mixed and dissolved in butylene glycol at 70° C. The resultant composition of step 2 is slowly added to the resultant composition of step 1, with mixing. This mixture is then cooled to its congealing point with mixing and then cooled to room temperature without mixing.

EXAMPLE 12

In this example a topical gel is prepared. As a first step, hydroxy propyl cellulose is hydrated and dissolved into water. As a second step, A compound of formula I or formula IV, or a mixture thereof, butylene glycol and PPG-12-

Buteth-16 are dissolved in alcohol. Slowly the resultant mixture of step 2 is added into the resultant mixture of step 1 with mixing until a gel forms.

TABLE 3

Amide and/or Bis-Amide Formulations

| Ingredients | Example 9 Topical Tincture % w/w | Example 10 Topical Cream/Lotion % w/w | Example 11 Topical Ointment % w/w | Example 12 Topical Gel % w/w |
|---|---|---|---|---|
| 1. Compound of formula I, formula IV, or a mixture thereof | 1.0 | 1.0 | 1.0 | 1.0 |
| 2. Methyl Paraben NF | — | .01 | — | — |
| 3. Propyl Paraben NF | — | .01 | — | — |
| 4. Hydroxy Propyl Cellulose (note 1) | — | — | — | 1.0 |
| 5. PPG-12-Buteth-16 (note 2) | — | — | — | 2.0 |
| 6. Squalane (note 3) | — | 2.0 | — | — |
| 7. Glyceryl Monostearate NF | — | — | 2.0 | — |
| 8. Stearyl Alcohol NF | — | 2.8 | — | — |
| 9. Cetyl Alcohol NF | — | 4.2 | — | — |
| 10. Polyethylene Glycol Cetyl Ether (note 4) | — | 5.0 | — | — |
| 11. Mineral Oil NF | — | 5.0 | — | — |
| 12. Butylene Glycol | 4.0 | — | 12.0 | 4.0 |
| 13. Petrolatum USP | — | 5.4 | 85.0 | — |
| 14. Alcohol (note 5) | 89.0 | — | — | 47.0 |
| 15. Water | 6.0 | 74.4 | — | 45.0 |
| | 100.0 | 100.0 | 100.0 | 100.0 |

Notes:
(1) available under the trademark Klucel ® from Hercules
(2) available under the trademark Ucon ® fluid 50 HB from Union Carbide
(3) available under the treademark Robane ® from Robeco
(4) available under the trademark Brij 58 ® from ICI

EXAMPLE 13

To examine the effect of the amides and bis-amides of the present invention on the skin, stratum corneum is used as a model to determine the degree in which the amides and bis-amides of the present invention effectively treat dry skin by increasing the extensibility thereof. Stratum corneum samples are first equilibrated to 44% relative humidity (RH) by suspending the samples over a saturated salt solution of potassium carbonate. After equilibration, the stratum corneum samples are extended by 2% of their original length at 20 mm/min using a linear extensometer. The amount of force required to extend the sample is computed and the information displayed as a force extension graph on a personal computer. The initial slope of the curve in the Hookean region is then used as an indicator of the integrity of the stratum corneum (gram-force/100% extension). 50 μl of the amide or bis-amide to be tested is then applied to the external surface of five pieces of stratum corneum samples and rubbed in with 20 strokes of a gloved finger. The samples are then equilibrated to 80% RH by suspending over a saturated salt solution of ammonium sulfate in humidity chambers and then incubated at this humidity for three hours. The samples are then reequilibrated to 44% RH and after conditioning, restretched to 2% extension. Results are then expressed as extensibility ratios of before/after treatment. The same test is run for 4% extension.

EXAMPLE 14

To the half an area of the face, neck, forearm, back or buttocks of each member of a panel of approximately 50 healthy volunteers is administered a composition comprising 0.01–5 wt. % of a compound of formula I or formula IV or mixture thereof and to the other half an area is administered a control composition. Applications are made once to 4 times daily for up to six months or more depending upon the condition to be treated. Panelists are assessed by expert assessors for overall improvement in the condition to be treated or the improvement in the texture and appearance of the skin.

The present invention is not to be limited in scope by the specific embodiments disclosed in the examples which are intended as illustrations of a few aspects of the invention and any embodiments which are functionally equivalent are within the scope of this invention. Indeed, various modifications of the invention in addition to those shown and described herein will become apparent to those skilled in the art and are intended to fall within the appended claims.

A number of references have been cited and the entire disclosures of which are incorporated herein by reference.

What is claimed is:

1. A compound of formula IV:

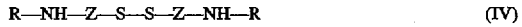

R—NH—Z—S—S—Z—NH—R        (IV)

or pharmaceutically or cosmetically acceptable salts thereof, wherein:

each R is independently selected from the group consisting of (A)(A)C(OH)—C(O)— and 2-(HO)$C_6H_4$C(O)—; wherein each A is independently selected from the group consisting of hydrogen, phenyl and a $C_1$–$C_{22}$ alkyl or alkenyl group, said $C_1$–$C_{22}$ alkyl or alkenyl group being optionally substituted with one or more $C_1$–$C_4$ alkyl groups, phenyl, halogen or hydroxyl groups, said phenyl being optionally substituted with one or more $C_1$–$C_4$ alkyl, halogen, hydroxyl groups or methoxyl group; and each Z is independently selected from the group consisting of $C_2$–$C_{12}$ alkyl, $C_2$–$C_{12}$ alkenyl and $C_2$–$C_{12}$ alkynyl.

2. The compound of claim 1, wherein R is selected from the group consisting of 2-hydroxyethanoyl; 2-hydroxypropanoyl; 2-methyl-2-hydroxypropanoyl; 2-hydroxybutanoyl; 2-hydroxypentanoyl; 2-hydroxynonanoyl; 2-hydroxydecanoyl; 2-hydroxyoctanoyl; 2-hydroxydodecanoyl; 2-hydroxytetradecanoyl; 2-hydroxyhexadecanoyl; 2-hydroxyoctadecanoyl; 2-hydroxyeicosanoyl; 2-hydroxyphenyl-2-hydroxyethanoyl; 2,2-diphenyl-2-hydroxyethanoyl; 3-phenyl-2-hydroxypropanoyl; 2-phenyl-2-methyl-2-hydroxyethanoyl; 2-(4'-chlorophenyl)-2-hydroxyethanoyl; 2-(4'-hydroxy-3'methoxyphenyl)-2-hydroxyethanoyl; 3-(2'-hydroxyphenyl)-2-hydroxypropanoyl; 3-(4,-hydroxyphenyl)-2-hydroxypropanoyl; 2-(3',4'-dihydroxyphenyl)-2-hydroxyethanoyl; and salicylyl; and Z is $C_2$–$C_6$ alkyl.

3. The compound of claim 1, wherein said compound is selected from the group consisting of:

N,N'-bis(salicylyl)cystamine;

N,N'-bis(lactyl)cystamine;

N,N'-bis(2-hydroxyoctanoyl)cystamine;

N,N'-bis(2-hydroxydecanoyl)cystamine; and

N,N'-bis(2-hydroxydodecanoyl)cystamine, or a pharmaceutically or cosmetically acceptable salt thereof.

4. A composition for treating a biological skin condition or disease selected from the group consisting of dry skin; severe dry skin; dandruff; acne; keratoses; psoriasis; eczema; skin flakiness; pruritus; age spots; lentigines; melasmas; coarse wrinkles; fine wrinkles; warts; blemished skin; hyperpigmented skin; hyperkeratotic skin; inflammatory dermatoses; skin in need of cleansers and skin atrophy, said composition comprising a pharmaceutically or cosmetically acceptable vehicle and a compound of claim 1.

5. The composition of claim 4 wherein said compound wherein said compound is selected from the group consisting of:

N,N'-bis(salicylyl)cystamine;

N,N'-bis(lactyl)cystamine;

N,N'-bis(2-hydroxyoctanoyl)cystamine;

N,N'-bis(2-hydroxydecanoyl)cystamine; and

N,N'-bis(2-hydroxydodecanoyl)cystamine, or a pharmaceutically or cosmetically acceptable salt thereof.

6. The composition of claim 4 wherein said compound is present in an amount of about 0.01 to about 5 wt. % of the composition.

7. The composition of claim 6 wherein said compound is present in an amount of about 0.05 to about 1.0 wt. % of the composition.

8. The composition of claim 4 wherein said vehicle is selected from the group consisting of lotions, tinctures, creams, emulsions, mousses, sprays, foams, powders, gels and ointments.

9. The composition of claim 4 wherein said composition is a topical composition.

10. A method for treating a biological skin condition or disease selected from the group consisting of dry skin; severe dry skin; dandruff; acne; keratoses; psoriasis; eczema; skin flakiness; pruritus; age spots; lentigines; melasmas; coarse wrinkles; fine wrinkles; warts; blemished skin; hyperpigmented skin; hyperkeratotic skin; inflammatory dermatoses; skin in need of cleansers and skin atrophy, in a patient in need of such treatment, which comprises topically administering to the patient on the area of skin having said condition or disease a composition comprising a pharmaceutically or cosmetically acceptable vehicle and a compound of claim 1.

11. The method of claim 10 wherein said compound is selected from the group consisting of:

N,N'-bis(salicylyl)cystamine;

N,N'-bis(lactyl)cystamine;

N,N'-bis(2-hydroxyoctanoyl)cystamine;

N,N'-bis(2-hydroxydecanoyl)cystamine; and

N,N'-bis(2-hydroxydodecanoyl)cystamine, or a pharmaceutically or cosmetically acceptable salt thereof.

12. The method of claim 10 wherein said compound is present in an amount of about 0.01 to about 5 wt. % of the composition.

13. The method of claim 12 wherein said compound is present in an amount of about 0.5 to about 1.0 wt. % of the composition.

14. The method of claim 10 wherein said compound is present in an amount of about 0.01 to about 5 wt. % of the composition.

15. The method of claim 14 wherein said compound is present in an amount of about 0.5 to about 1.0 wt. % of the composition.

16. The method of claim 10 wherein said vehicle is selected from the group consisting of lotions, tinctures, creams, emulsions, mousses, sprays, foams, powders, gels and ointments.

17. The composition of claim 4 further comprising one or more alpha- or beta-hydroxyacids selected from the group consisting of lactic mid, glycolic acid, citric acid, alpha-hydroxyoctanoic acid, alpha-hydroxydecanoic acid, alpha-hydroxylauric acid, tartaric acid, glucouronic acid, galactouronic acid, alpha-hydroxybutyric acid, alpha-hydroxyisobutyric acid, malic acid, mandelic acid, pyruvic acid, tartronic acid, and salicylic acid, and esters, thioesters, amides and lactones thereof.

18. The method of claim 10, wherein the composition further comprises one or more alpha- or beta-hydroxyacids selected from the group consisting of lactic acid, glycolic acid, citric acid, alpha-hydroxyoctanoic acid, alpha-hydroxydecanoic acid, alpha-hydroxylauric acid, tartaric acid, glucouronic acid, galactouronic acid, alpha-hydroxybutyric acid, alpha-hydroxyisobutyric acid, malic acid, mandelic acid, pyruvic acid, tartronic acid, and salicylic acid, and esters, thioesters, amides and lactones thereof.

* * * * *